US008856188B2

(12) United States Patent
Reiner (10) Patent No.: US 8,856,188 B2
(45) Date of Patent: Oct. 7, 2014

(54) ELECTRONIC LINKAGE OF ASSOCIATED DATA WITHIN THE ELECTRONIC MEDICAL RECORD

(76) Inventor: Bruce Reiner, Berlin, MD (US)

(*) Notice: Subject to any disclaimer, the term of this patent is extended or adjusted under 35 U.S.C. 154(b) by 437 days.

(21) Appl. No.: 12/659,363

(22) Filed: Mar. 5, 2010

(65) Prior Publication Data

US 2010/0235330 A1   Sep. 16, 2010

Related U.S. Application Data

(60) Provisional application No. 61/202,571, filed on Mar. 13, 2009.

(51) Int. Cl.
*G06F 17/30* (2006.01)
*G06F 19/00* (2011.01)

(52) U.S. Cl.
CPC ........ *G06F 17/30595* (2013.01); *G06F 19/322* (2013.01)
USPC ............ 707/802; 707/705; 707/791; 707/812

(58) Field of Classification Search
CPC .................. G06F 17/30595; G06F 17/30672; G06F 17/30938; G06F 17/30979; G06F 19/322; Y10S 707/99933; Y10S 707/99945; Y10S 707/99941
USPC ......................... 707/705, 802, 690, 791, 812
See application file for complete search history.

(56) References Cited

U.S. PATENT DOCUMENTS

| | | | | |
|---|---|---|---|---|
| 5,911,687 A * | 6/1999 | Sato et al. | | 600/300 |
| 7,080,098 B2 * | 7/2006 | Smirniotopoulos et al. | | 707/781 |
| 7,401,028 B2 * | 7/2008 | Deakter | | 705/3 |
| 7,647,320 B2 * | 1/2010 | Mok et al. | | 707/770 |
| 7,720,693 B2 * | 5/2010 | Funahashi et al. | | 705/2 |
| 7,774,377 B2 * | 8/2010 | Schoenberg | | 707/803 |
| 7,805,377 B2 * | 9/2010 | Felsher | | 705/64 |
| 7,933,782 B2 * | 4/2011 | Reiner | | 705/2 |
| 2002/0004727 A1 * | 1/2002 | Knaus et al. | | 705/3 |
| 2002/0038378 A1 * | 3/2002 | Simmon et al. | | 709/234 |
| 2003/0013951 A1 * | 1/2003 | Stefanescu et al. | | 600/407 |
| 2003/0050803 A1 * | 3/2003 | Marchosky | | 705/3 |
| 2003/0140044 A1 * | 7/2003 | Mok et al. | | 707/10 |
| 2003/0154105 A1 * | 8/2003 | Ferguson | | 705/2 |
| 2004/0122703 A1 * | 6/2004 | Walker et al. | | 705/2 |
| 2004/0122790 A1 * | 6/2004 | Walker et al. | | 707/1 |
| 2004/0254816 A1 * | 12/2004 | Myers | | 705/2 |
| 2004/0260658 A1 * | 12/2004 | Dettinger et al. | | 705/400 |
| 2005/0108055 A1 * | 5/2005 | Ott et al. | | 705/2 |
| 2006/0235836 A1 * | 10/2006 | Dettinger et al. | | 707/4 |
| 2006/0241977 A1 * | 10/2006 | Fitzgerald et al. | | 705/3 |
| 2006/0271400 A1 * | 11/2006 | Clements et al. | | 705/2 |
| 2007/0299697 A1 * | 12/2007 | Friedlander et al. | | 705/3 |
| 2008/0126134 A1 * | 5/2008 | Jones et al. | | 705/3 |
| 2008/0126277 A1 * | 5/2008 | Williams et al. | | 706/14 |
| 2008/0243885 A1 * | 10/2008 | Harger et al. | | 707/100 |
| 2008/0288466 A1 * | 11/2008 | Eisenberger et al. | | 707/3 |
| 2009/0089095 A1 * | 4/2009 | Esham et al. | | 705/3 |
| 2009/0177492 A1 * | 7/2009 | Hasan et al. | | 705/3 |
| 2010/0287213 A1 * | 11/2010 | Rolls et al. | | 707/803 |
| 2014/0037162 A1 * | 2/2014 | Papier et al. | | 382/128 |

* cited by examiner

*Primary Examiner* — Thanh-Ha Dang (57) ABSTRACT

The present invention provides a mechanism to define an association between different data elements from disparate sources of data and databases, and different database elements, and track that association over time. This mechanism track multiples related data elements throughout the continuum of an individual patient's medical record and identifies consistent data relationships across large patient populations.

24 Claims, 2 Drawing Sheets

ELECTRONIC LINKAGE OF ASSOCIATED DATA WITHIN THE ELECTRONIC MEDICAL RECORD

CROSS-REFERENCE TO RELATED APPLICATIONS

The present application claims priority from U.S. Provisional Patent Application No. 61/202,571, filed Mar. 13, 2009, the contents of which are herein incorporated by reference in its entirety.

BACKGROUND OF THE INVENTION

In current medical practice, a patient's electronic medical record (EMR) consists of multiple data elements from a number of clinical, imaging, and laboratory databases which are distinct and separate. The ability to correlate data from one database to another is extremely limited and for the most part, manual, and does not lend itself to automated analysis, due to the inability of these databases to be dynamically combined.

SUMMARY OF THE INVENTION

The present invention provides a mechanism to define an association between different data elements from disparate sources of data and databases, and different database elements, and track that association over time. The present invention provides a mechanism to track multiple related data elements throughout the continuum of an individual patient's medical record and identify consistent data relationships across large patient populations.

In one embodiment consistent with the present invention, different data elements having various relationships or associations with one another, in a medical application, such as a radiologist reviewing a medical image and associating data elements on that image with the patient electronic medical record (EMR), will have the association relationships explicitly defined by the user, between the two different data elements. The association relationship is electronically "linking" between the two data elements through an input device (e.g., electronic stylus, mouse, keyboard), with an author-defined association relationship. Any specific data element whether in the clinical electronic medical record or imaging-related, could have any number of associations with any other elements, and these associations could be made by any number of physicians, other healthcare workers or other observers and consequently could support multiple associations some of which might be consistent and some inconsistent among various observers (associators).

In addition to defining the specific type of association, the author (observer or associator) also inputs the strength of the relationship. These author-derived association data are then recorded by the user or the program in an "association database" or alternatively, in an "association service". When a new association is identified by a user, the program would have the association service automatically add this association to the database and make the association available to other programs (i.e., different medical information systems databases—e.g., RIS, HIS, EMR, PACS), and would also index the association in the database. Thus, any time the user accesses data relative to that specific patient (or another patient with similar data), the association would be displayed for review.

The user has the option to modify any previously defined association relationships, in keeping with the new data and his/her own knowledge. Any modifications to the association data are recorded in the association database and attributable to the specific author. These association relationships can be analyzed by the program at a later date as additional clinical data and knowledge is gained by a variety of decision support or other programs. In this manner, knowledge and intelligence are built up by virtue of these associations which assess the certainty, strength and type of associations, in addition to other parameters.

The author of the association data (e.g., radiologist) can create his/her own user and context-specific association profiles, which can define which data sources are of highest priority under specific circumstances.

Additionally, standardized association templates could help to make presumptive associations based on knowledge from the general medical, surgical, or sub-specialty literature. As the association database becomes populated with large amounts of data (which is correlated with diagnosis), artificial intelligence techniques (e.g., neural networks) can be utilized to create computer program-derived association links.

In another embodiment consistent with the present invention, one aspect is the ability to cross-reference association databases from multiple institutions. Once the data is recorded in a standardized fashion in a database, these data can be merged by the program from various such databases, to provide larger statistical sample sizes.

In the event two authors differ on their perceived association relationships, the program will record both individual author's observations. Whenever the data is accessed at the client computer by a new end-user, the opposing data will be presented/displayed by the program and the new authors will be provided with the option of recording their own opinions as to the association relationship. Whenever conflicting data is recorded by the program, an automated alert will be sent or made available by the program (according to preset communication protocols, like fax, email, etc.) to the corresponding authors, who will be provided with the option of amending their original data entry or maintaining it "as is". As long as an association has been recorded by the program, this association will appear in the association database (but annotated as a source of discrepancy by the program).

When a definitive diagnosis has been established, the discrepant association data will be reviewed and analyzed for accuracy using the program's artificial intelligence (or manual review). This review data and analysis will be recorded by the program in the final association database and quantitative measures of diagnostic accuracy (for all individual authors) will reflect any identified discrepancies.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
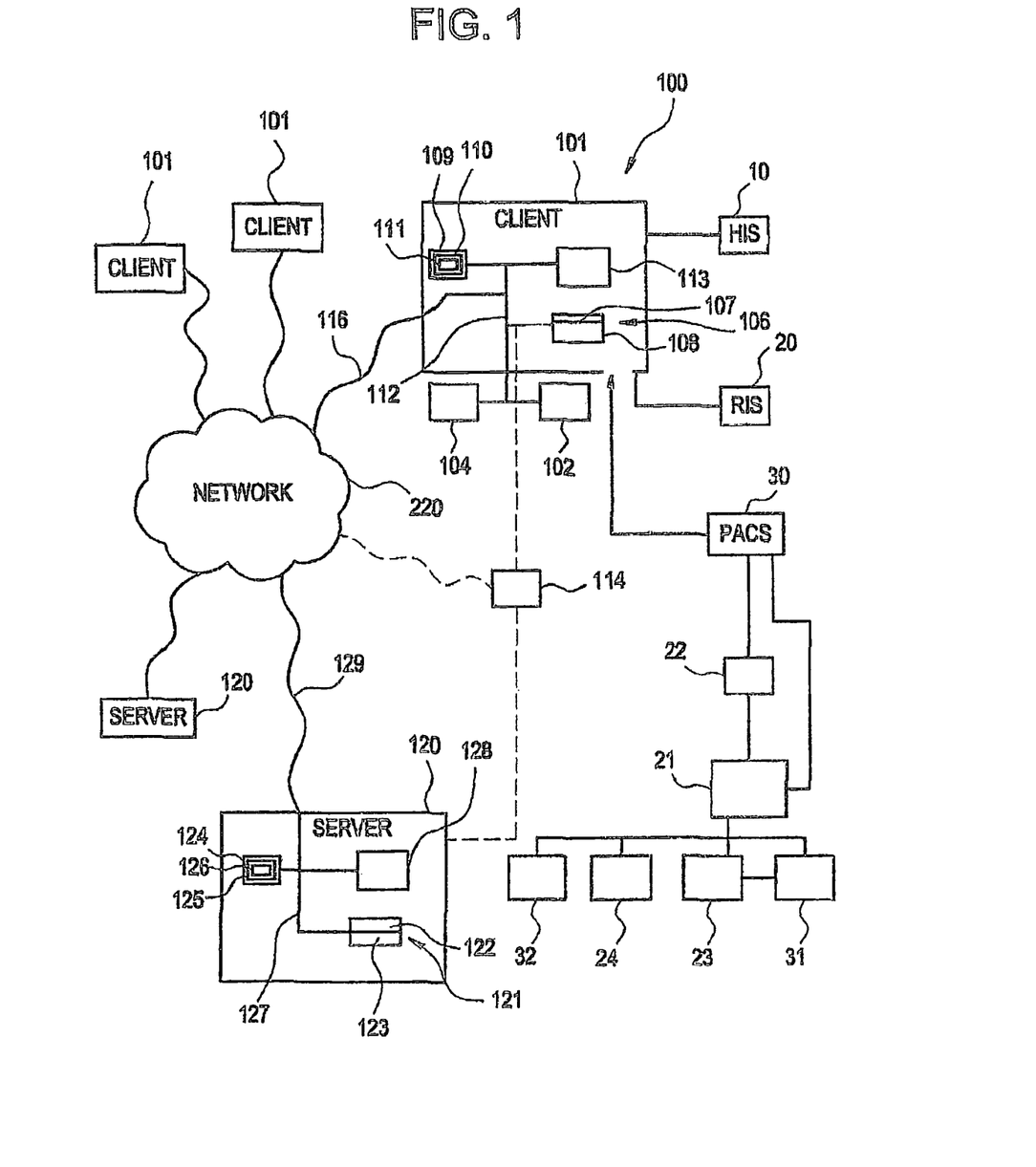
FIG. 1 is a schematic drawing of the major components for tracking the association between different data elements from disparate sources of data and databases, and different database elements, over time, throughout the continuum of an individual patient's medical record.

According to one embodiment of the invention, as illustrated in FIG. 1, the major components of a methodology for tracking the association between different data elements from disparate sources of data and databases, and different database elements, over time, throughout the continuum of an individual patient's medical record, may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, perhaps an eye movement detection apparatus 300, the electronic medical record (EMR), computer-aided detection (CAD), and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, radiographic device 21, CR/DR plate reader 22, PACS 30, and eye movement detection apparatus 300, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely. According to another embodiment of the invention, the client computers 101 may include several components, including processors, RAM, a USB interface, a telephone interface, microphones, speakers, a computer mouse, a wide area network interface, local area network interfaces, hard disk drives, wireless communication interfaces, DVD/CD readers/burners, a keyboard, and/or other components. According to yet another embodiment of the invention, client computers 101 may include, or be modified to include, software that may operate to provide data gathering and data exchange functionality.

According to one embodiment of the invention, an input device 104 or other selection device, may be provided to select hot clickable icons, selection buttons, and/or other selectors that may be displayed in a user interface using a menu, a dialog box, a roll-down window, or other user interface. In addition or substitution thereof, the input device may also be an eye movement detection apparatus 300, which detects eye movement and translates those movements into commands.

The user interface may be displayed on the client computer 101. According to one embodiment of the invention, users may input commands to a user interface through a programmable stylus, keyboard, mouse, speech processing device, laser pointer, touch screen, or other input device 104, as well as an eye movement detection apparatus 300.

According to one embodiment of the invention, the client computer system 101 may include an input or other selection device 104, 300 which may be implemented by a dedicated piece of hardware or its functions may be executed by code instructions that are executed on the client processor 106. For example, the input or other selection device 104, 300 may be implemented using the imaging display device 102 to display the selection window with an input device 104, 300 for entering a selection.

According to another embodiment of the invention, symbols and/or icons may be entered and/or selected using an input device 104 such as a multi-functional programmable stylus 104. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS 30 and Electronic Medical Report (EMR).

In one embodiment consistent with the present invention, the eye movement detection apparatus 300 that is used as an input device 104, may be similar to the Eye-Tracker SU4000 (made by Applied Science Laboratories, Bedford, Mass.) with head-tracking capability. However, other types of eye tracking devices may be used, as long they are able to compute line of gaze and dwell time with sufficient accuracy.

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, 300, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the client computer 101 may include an image display device 102 which may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, the PACS 30 (if separate), and the eye movement detection apparatus 30, are shown as directly coupled to the client computer 101, it is known that these systems may be indirectly coupled to the client over a LAN, WAN, the Internet, and/or other network via communication links. Further, even though the eye movement detection apparatus 300 is shown as being accessed via a LAN, WAN, or the Internet or other network via wireless communication links, it is known that the eye movement detection apparatus 300 could be directly coupled using wires, to the PACS 30, RIS 20, radiographic device 21, or HIS 10, etc.

According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition or eye movement detection. According to one embodiment, user interfaces may be provided that support several interfaces including display screens, voice recognition systems, speakers, microphones, input buttons, eye movement detection apparatuses, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system or eye movement detection apparatus 300 to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

In one embodiment consistent with the present invention, different data elements will have various relationships or associations with one another. For example, in a medical application, such as a radiologist reviewing a medical image and associating data elements on that image with the patient electronic medical record (EMR), a number of different associations may exist among the different data elements, including relationships such as: 1) equivalence, 2) "connected to", 3) "becomes" (temporal association), 4) "approximates", 5) causation, and 6) "unrelated to".

When one data element is encountered, which appears to be related to another data element, the individual end-user has the opportunity to explicitly define an association relationship between the two different data elements. Continuing the radiologist example, a radiologist interpreting a chest radiograph my identify a focal abnormality (e.g., mass) and define a relationship between that finding on an image (e.g., mass)

and a clinical data element described in the patient history and physical report (e.g., chronic cough). In this particular example, the radiologist may determine the associative relationship is one of causation (i.e., the mass is causing the chronic cough).

The radiologist can record this association relationship by electronically "linking" the two data elements through an input device (e.g., electronic stylus, mouse, keyboard). In the case of the stylus as an input device, the radiologist could circle the words "mass" (from the radiology report) and "chronic cough" from the history and physical report and record and store the association function using text or a particular symbol (e.g., graphical symbol for association) in the database 113, 114. This mass, in turn, could be associated by the user with other findings or other observations in the clinical patient record or could be associated with a future similar finding on a future radiology examination.

An alternative input would be through the use of a computer mouse or input device 104 where each data element can be highlighted and then associated, for example, through the Shift/Tab function of the keyboard.

In either scenario, the two data elements from two different data sources become electronically "linked" with an author-defined association relationship. Any specific data element whether in the clinical electronic medical record or imaging-related, could have any number of associations with any other elements, and these associations could be made by any number of physicians, other healthcare workers or other observers and consequently the system 100 could support multiple associations some of which might be consistent and some inconsistent among various observers (associators).

In addition to defining the specific type of association, the author (observer or associator) also inputs the strength of the relationship (i.e., how closely the two data elements are associated with one another), such as "possibly associated", "likely associate", or "definitely associated", and also, how the data are associated (i.e., is there a "cause and effect relationship" or are they "essentially equivalent", or are they "definitely different", etc.). In the above radiologist example, the radiologist might determine that the strength of the association would be classified as "likely associated".

These author-derived association data are then recorded by the user or the program 110 in an "association database" 113, 114 or alternatively, in an "association service" which could be a web service which would cut across multiple databases 114 and potentially multiple information systems in multiple facilities, which would record a variety of data elements, such as (but not limited to): 1) data elements defining the association relationship; 2) data sources of these data elements; 3) type of association relationship; 4) strength of association relationship; 5) author of the defined association relationship; 6) date and time of data recording; 7) degree of database 114 concurrence (i.e., a computer program-generated statistical analysis); 8) previously defined association data; and 9) response to computer program-derived association relationships.

The data entered into the association database 114 could be standardized by the program 110 using, for example an established XML schema, so as to ensure that all association data complies with one or more established industry-wide standards, thereby providing a mechanism for meta-analysis of multiple association databases 114.

When a new association is identified by a user, the program 110 would have the association service automatically add this association to the database 114 and make the association available to other programs (i.e., different medical information systems databases—e.g., RIS, HIS, EMR, PACS), and would also index the association in the database 114. Thus, any time the user accesses data relative to that specific patient (or another patient with similar data), the association would be displayed for review.

The program 110 would generate a query to identify any other pre-defined association relationships relating to the specific data elements being linked. In this example of the mass (on the chest radiograph report) and chronic cough (on the history and physical report), a previously recorded association relationship may have been recorded for "chronic cough" (H & P) and "elevated white blood cell count" (laboratory report). In this example, the author might have reported an association of "connected to" and "likely associated".

When this data is presented/displayed by the program 110 to the radiologist or other interpreting/reading/treating physician for example, he/she has the option to modify any previously defined association relationships, in keeping with the new data and his/her own knowledge. Any modifications to the association data are recorded in the association database 114 by the program 110 and attributable to the specific author. These association relationships can be analyzed by the program 110 at a later date as additional clinical data and knowledge is gained by a variety of decision support or other programs. In this manner, knowledge and intelligence are built up by virtue of these associations which assess the certainty, strength and type of associations, in addition to other parameters.

In this example, if the patient was to have surgery for the mass in question, the pathology results (which are defined as "truth") would provide a mechanism for the program 110 to retrospectively correlate the association data, and if appropriate, serve as a gold standard to evaluate the validity of the associations made in the diagnostic process. These quantitative analyses (determining association accuracy) could then be presented or displayed by the program 110 to each individual author for retrospective review and be prospectively used for developing computerized artificial intelligence in the creation of automated association relationships by utilizing a Bayesian analysis and a variety of other statistical techniques.

The author of the association data (e.g., radiologist) can create his/her own user and context-specific association profiles, which can define which data sources are of highest priority under specific circumstances. Examples of the various data sources available within the patient EMR for data mining include: 1) history and physical (H & P); 2) progress notes; 3) consultation reports; 4) operative notes; 5) laboratory data; 6) pathology reports; 7) radiology reports; 8) procedural reports; 9) genomic and proteomic data; 10) pharmacology; 11) physician orders; and 12) medical problem lists.

The radiologist may create his/her own user-specific profile to prioritize association data from imaging reports, laboratory data, pathology reports, and medical problem lists etc. By doing so, whenever that radiologist creates new association data relationships, he/she is presented by the program 110 with pre-defined association relationships of these data elements from preferred data sources. In this example, the data element "chronic cough" (from the H & P) may have a number of previously reported association links including the following:

1. Symptomatic improvement after oxygen therapy (Progress note)
2. Multiple allergies (Pulmonary consultation report)
3. Respiratory function studies (Procedural report)
4. Antibiotic therapy and bronchodilators (Pharmacology)
5. Sputum culture (Lab/Microbiology)
6. COPD, unexplained weight loss (Medical problem list)

By defining their own context and user-specific association profile, the radiologist creates a mechanism to prioritize association data. This creates an effective filter so that the amount of association data presented or displayed by the program 110 to him/her is streamlined, in accordance to his/her own clinical requirements. As this historical association data is presented/displayed to the radiologist by the program 110, he/she can manually incorporate any of these pre-defined association data into his/her newly formed association link (using the same workflow and input previously described).

In this continuing example, the radiologist elects to link the "sputum culture" and "unexplained weight loss" data with the newly identified "mass" and "chronic cough" data. If that radiologist were to open up that specific patient's medical record on the computer 101 in the future, these pre-defined association data will be automatically presented/displayed by the program 110. At the same time, when the definitive diagnosis is realized (e.g., lung cancer), the radiologist will be notified electronically by the program 110 (by communication means preset, such as email, fax, etc.), and provided with the relevant data (via display) and review. This would include the radiologist-defined association data, diagnosis, and additional association data demonstrated to be of high clinical significance. This provides an effective education/training tool for all end-users, so that all defined association data can be reviewed and analyzed at the time of diagnosis by the program 110, along with individual end-users quantitative measures of diagnostic accuracy.

Additionally, standardized association templates could help to make presumptive associations based on knowledge from the general medical, surgical, or sub-specialty literature. For example, allergic responses and drug reactions can be stored in the database 114 of the system 110 and subsequent findings, symptoms, etc., could be used to establish a possible relationship. A knowledge database 114 about findings and symptoms associated with various diseases, complications associated with surgery, and imaging findings associated with certain disease processes could help the program 110 to form automated "associations", that could be supplemented by physicians and other healthcare workers, for example, when they made new associations or confirmed or failed to confirm possibilities suggested by the program 110. This knowledge and these associations could cut across multiple disparate information systems so that a presentation of cough and fever at an ER at a hospital could be associated with an elevated white blood cell count and lung parenchymal consolidation noted at another facility and the diagnosis of pneumonia.

As the association database 114 becomes populated with large amounts of data (which is correlated with diagnosis), artificial intelligence techniques (e.g., neural networks) can be utilized to create computer program-derived association links. If, for example, the radiologist fails to recognize an association relationship between mass (radiology report) and chronic cough (H & P), the program 110 may provide an electronic prompt to the radiologist to alert him/her as to the possibility of an overlooked association. When the data is presented/displayed to the radiologist, the program 110 will present the associated data elements, source of the data, and type/strength of the association relationship. The end-user can in turn elect to accept the program-derived association (i.e., "as is"), modify the program-derived association, or reject the program-derived association. Whatever actions are taken by the end-user in response to the program 110 prompt will be recorded by the program 110 in the database 114, to assist with future end-user education and refinement of the program-based algorithms.

In another embodiment consistent with the present invention, an important aspect is the ability to cross-reference association databases 114 from multiple institutions. Once the data is recorded in a standardized fashion in a database 114, these data can be merged by the program 110 from various such databases 114, to provide larger statistical sample sizes.

Because manual data input is an important source of association data, it will be typical for different authors to have varying opinions as to the presence and type of data associations. The association database 114 will store the author of the association data and the program 110 will provide a feedback mechanism when conflicting association data is recorded. Whenever an author is presented by the program 110 with pre-defined association data, he/she can elect to agree or disagree with the recorded data:

1. Author agrees with pre-defined association relationship.
2. Author disagrees with pre-defined association relationship:
   a. No association exists.
   b. Association exists, but differs from recorded type of association relationship.
   c. Association exists, but differs in the reported strength of association.

In the event where two authors differ on their perceived association relationships, the program 110 will record both individual author's observations. Whenever the data is accessed at the client computer 101 by a new end-user, the opposing data will be presented/displayed by the program 110 and the new authors will be provided with the option of recording their own opinions as to the association relationship. Whenever conflicting data is recorded by the program 110, an automated alert will be sent or made available by the program 110 (according to preset communication protocols, like fax, email, etc.) to the corresponding authors, who will be provided with the option of amending their original data entry or maintaining it "as is". As long as an association has been recorded by the program 110, this association will appear in the association database 114 (but annotated as a source of discrepancy by the program 110).

When a definitive diagnosis has been established, the discrepant association data will be reviewed and analyzed for accuracy using the program's 110 artificial intelligence (or manual review). This review data and analysis will be recorded by the program 110 in the final association database 114 and quantitative measures of diagnostic accuracy (for all individual authors) will reflect any identified discrepancies.

The ability to review association data and all relevant source data is especially beneficial, as it relates to longitudinal analysis and end-user workflow. In the previously cited example of the mass (chest radiograph report) and chronic cough (H & P), a number of actions can take place in response to the data at hand. The chest radiographic finding of mass may elicit the recommendation from a user, or by the program 110, for a chest CT to better characterize the mass in question. The resulting chest CT report may provide additional association data by describing the mass in greater detail based upon the enhanced diagnostic capabilities of CT as compared with chest radiography. For example, the chest CT report may record specific volumetric and density measurements of the mass, a differential diagnosis, and recommendation for biopsy. Since the recommendation for biopsy will generate an interventional procedure (e.g., bronchoscopy) and pathologic diagnosis, the resulting data can be automatically linked by the program 110 with the original data source (chest CT mass), and automatic feedback can be directed by the program 110 to the original author of the association data (radiologist interpreting the chest CT report). This creates a mechanism for retrospective and prospective data linkage, along with automated feedback by the program 110.

Depending upon the individual end-user profile, the type of source data for review may be different. In the same example, five different end-users may want to review association data relevant to the CT defined mass. Based upon their own specific profile, the source data presented/displayed by the program 110 to the end-users for review may be far different, and may include, for example:

a. Primary care physician—Profile calls for annotated axial CT images demonstrating the mass in question, with direct linkage to the chest radiographic images.
b. Operating room nurse—Profile calls for AP chest radiographic image displaying right/left markers to identify mass laterality and corresponding chest CT report textual data reporting mass dimensions.
c. Surgeon—Profile calls for 3-D reconstructions of chest CT dataset to demonstrate volumetric measurements of mass and relationship to critical anatomic structures (e.g. pulmonary arteries).
d. Pathologist—Profile calls for chest CT images with volumetric measurements of primary tumor and regional hilar/mediastinal lymph nodes.
e. Radiation technologist—Profile calls for 2-D reconstructions in sagittal and coronal planes to determine tumor volume and linear measurements from skin surface to tumor epicenter.

The above illustrates the fact that based upon the specific end-user profile, the linked association data presented/displayed to each end-user by the program 110 is different in accordance with occupational and experiential differences. As a result, the association database 114 defines different levels of source data requirements for each data element recorded.

Figure 2:
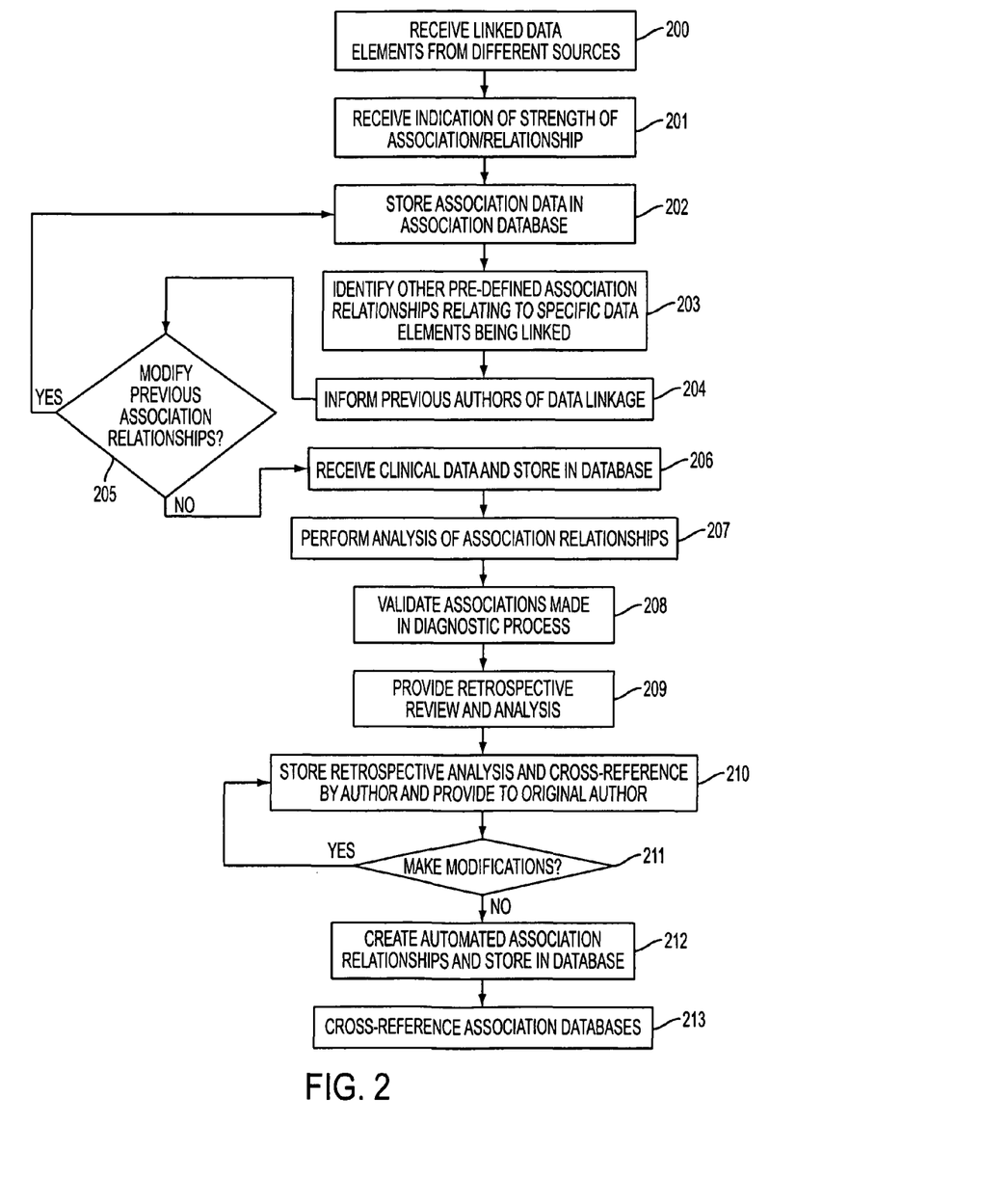
FIG. 2 is a flowchart showing the major steps involved in tracking the association between different data elements from disparate source of data and databases, and different database elements, in a medical application.

Specific features of the present invention include, but are not limited to, the following steps, as shown in FIG. 2:

Step 200: The program 110 of the electronic system 100 receives linked multiple data elements, through different user input mechanisms and from different sources.

Step 201: Once the linkage of data is determined by the end-user, the program 110 receives the end-user identification of the specific type of association relationship between the data elements as well as their own diagnostic confidence in the data association.

Step 202: This data is then recorded by the program 110 in an association database 114 (may be a dedicated database 114), where the program 110 tracks all "linked" data elements and their relationship to the specific underlying pathology.

Step 203: Whenever any of the associated data are reviewed by a user, or by the program 110 in an automatic review/analysis function, the corresponding associated data elements (and their pre-defined association relationships relating to specific data elements being linked) are displayed to the end-user. In this way, a story line is established which links multiple data elements (each from their own respective database 114) across the individual patient's medical record continuum.

Step 204: As new association data is recorded by the program 110, a feedback loop is created by the program 110 where the original author of the association data linkage is informed of newly associated data by a predetermined communications protocol (i.e., fax, email, etc.).

Step 205: If the association data differs from the previously recorded data, the program 110 will forward a query to the user and the original author regarding whether the association relationships should be modified. If so, the data is modified and stored as in step 202. If not, then the user can move on to obtaining the clinical data.

Step 206: As clinical diagnoses are realized (through medical treatment, pathology, laboratory analysis, surgery) the clinical data is stored by the program 110.

Step 207: Analysis of the association relationships are performed by the program 110, with respect to the clinical data, including cross-reference of the recorded associated data elements, to better delineate association relationships.

Step 208: The results of the cross-reference of the recorded associated data elements with the established diagnosis by the program 110 is used by the program 110 to validate the associations made in the diagnostic process.

Step 209: Retrospective analysis of the recorded association data can in turn be performed manually or through program 110 artificial intelligence techniques, to better characterize the association relationships. At the time of the retrospective association data review, each end-user is provided by the program 110 with the option to incorporate the association data defined as "truth" into their own end-user profiles, so that if/when similar data is encountered in the future, the program 110 will provide an automated prompt identifying this association relationship.

Step 210: This retrospective analysis is then recorded and cross-analyzed by the program 110 with the association input data attributable to each individual author, and presented/displayed by the program 110 to the original author for review.

Step 211: The program 110 then determines if any modifications are received, and stores the modifications as in step 210.

Step 212: The association database 114 is used by the program 110 to create artificial intelligence programs, which can create automated association relationships, and provide automated prompts to the end-user at the time new data is recorded.

Step 213: These association databases 114 can utilize standardized data elements (in an XML schema) when the program 110 records, tracks, and analyzes all association data. In this way, the standardized association data can be cross-referenced or correlated by the program 110 with association databases 114 from multiple institutions, creating a mechanism for meta-analysis.

Medical education programs can be developed by the program 110 from the association database(s) 114 to develop context and user-specific educational programs.

When different end-users provide conflicting association data, the program 110 recognizes same from a comparative data analysis, and an electronic alert is sent by the program 110 (according to preset communication protocols like email, fax, etc.) to all authors who have contributed relevant association data, in an attempt to establish association consensus.

The program 110 also provides a "drop and drag" type of feature on the display 102 when populating progress notes, admission notes, discharge summaries, operative reports, imaging and lab reports etc. Each time a new note is written by a user, data from multiple sources within or outside the electronic medical record of a specific healthcare enterprise, are used by the program 110, wherever possible, to automatically populate the information in the note or observation or recommendation or consult etc. Consequently each of these notes or observations in the electronic medical record builds from prior observations, problem lists, lab or imaging studies, or other observations.

Thus, a new progress note for example, would include a combination of multiple previous observations, results etc., which would be associated without each of the notes having to serve as its own new "island" of information. Notes could then be associated with each other and shortened and constructed from concepts that would include prior associations, results, observations, complications, findings, etc. Concepts such as improvement over time, worsening over time, additional information supporting an observation or tentative diagnosis, issues related to specific patient problems could all be associated by the program 110, as new entries into the electronic medical record are made.

Decision support features can be combined with the present invention in order to provide additional assistance to the user. In one embodiment, the association database 114 can be queried by the program 110 in an attempt to identify new association relationships. This can be initiated by an individual practitioner by entering the individual word/s of interest and prompting the program 110 to access the association database 114 to identify additional association relationships. The program 110 would in turn correlate the data input with previously defined association relationships and prompt the end-user with a list of data elements which have identified association relationships with the input data.

As an example, if an ER physician was to input "diaphoresis and chest pain", the program 110 would retrieve data elements from the association databases 114 which have recorded association relationships with these terms. Since multiple association relationships exist, the program 110 would request that the end-user specify the specific type of association relationship of interest from among several categories of medical data, such as: 1) signs; 2) symptoms; 3) disease; 4) diagnostic testing; 5) treatment; 6) prevention; 7) demographics; and 8) lifestyle.

Thus, the program 110 would provide a pop-up menu on the display 102 which would request that the end-user specify the category of interest. If the end-user was to select "Disease", a list of diseases which are associated with "diaphoresis and chest pain" would be presented/displayed by the program 110, in hierarchical order, for example, based upon the overall strength (i.e., statistical probability) of the association. If the end-user was to select a disease from the presented list (e.g., myocardial infarction), the program 110 could then generate an additional query of the databases 114 for association links related to that specific disease state.

In this example, the ER physician queries the database 114 for "Diagnostic Testing" associated with myocardial infarction. The program 110 then provides a list of diagnostic tests on the display 102, shown to have association relationships with myocardial infarction, which are ranked in hierarchical order, based upon the strength of the association. Within the category of "Diagnostic Testing", a number of sub-categories are presented/displayed by the program 110, which include: a) laboratory; 2) pathology; 3) clinical; 4) imaging; and 5) molecular.

The ER physician then selects "laboratory" test, and is provided by the program 110 with a hierarchical list of laboratory tests shown to have association relationships with myocardial infarction. By utilizing this decision support feature of the program 110, the ER physician can gain knowledge to facilitate improved diagnosis, clinical management, and treatment.

Another decision support feature of the program 110 is the ability to search for unrecognized associated data within a given patient's electronic medical record (EMR). In this application, artificial intelligence and natural language processing tools can be used by the program 110 to correlate data within the patient's EMR, with multi-institutional association databases 114. These multi-institutional databases 114 represent co-mingling of numerous association databases 114, thereby providing the ability to acquire knowledge and perform meta-analysis over large statistical samples.

By querying a multi-institutional association database 114, all documented association relationships can be identified by the program 110 relative to the provided data input (i.e., diaphoresis and chest pain). In the example, the ER physician can narrow the search by selecting the category "symptoms". As the list of symptoms with association relationships is retrieved by the program 110 from the databases 114, the "Search" function of the program 110 is invoked. In the "Search" function, natural language processing of the program 110 is used to cull the patient EMR for any documented data with defined association relationships. In this particular example, the "Search" function has identified the term "shortness of breath" four times in the patient EMR and presented them to the user, on the display 102. The ER physician can review the specific records in which this data was recorded by invoking the "Retrieve" function.

Alternatively, if the ER physician had selected the category of "diagnostic testing", followed by a "Search" command, he/she would have learned from the program 110, that the association link of "EKG" was found in the patient's medical record on two separate occasions. By invoking the "Retrieve" function, the ER physician would be able to review on the display 102, the EKG results as retrieved by the program 110 from the database 114, along with other data recorded at the time these tests were performed. By utilizing this decision support feature of the association database 114, end-users can identify association data points not realized, and in turn search for these association links within the patient's medical record. Without the ability to automatically search the patient's record, many of these association data would go unrealized.

As noted above, The integration of data within multiple institutional databases 114 can provide for automated validation and refinement of association data. Using artificial intelligence and statistical methodology on pooled association data, the frequency, strength, and categorization of association relationships can be better defined. In addition, an institution (or individual practitioner) can export or import data from its own association database 114 with that of another institution (or individual practitioner).

In another embodiment consistent with the present invention, the program 110 can also be used to enhance diagnosis, clinical management, and treatment of individual patients by correlating generic association data (derived from the association database 114) with personalized data derived from an individual patient's genetic data. In the previously cited example of the ER physician inputting "diaphoresis and chest pain", and generating a "Search" query for "Disease", a list of diseases associated with the "symptoms" "diaphoresis and chest pain" will be presented/displayed following an automated search of the association database 114 by the program 110. This list of associated diseases will be ranked in hierarchical order, along with a statistical probability, based upon statistical analysis of the generic association database 114 by the program 110. If the ER physician wanted to add another category of association data (e.g., lifestyle) to assist in the diagnostic process, he/she could do so by adding this data (e.g., smoking history, high fat diet) to the analytical process. This added association data could then further refine the statistical analysis of differential diagnosis by the program 110.

An even more powerful method of combining generic and patient-specific association data to enhance medical knowledge and problem solving is through the addition of an individual patient's genetic data to association data analysis. In this example, the following steps would take place:

Step 300: The ER physician examines the patient and takes a history.

Step 301: The ER physician identifies symptoms which are believed to be definitely associated with one another (diaphoresis and chest pain), and related to the patient's presentation.

Step 302: The ER physician enters this association data in the computer 101 under the category of "Symptoms".

Step 303: The ER physician generates a "Retrieve" query of the association database 114 by the program 110 (selecting the multi-institutional databases 114), by selecting the "Disease" category for analysis.

Step 304: The program 110 in turn prompts the ER physician to enter additional association data he/she may feel is beneficial to the analysis.

Step 305: The ER physician is provided three options by the program 110 in his/her response:
  a. The ER physician requests the association analysis to be performed "as is" (i.e., no additional data).
  b. The ER physician manually enters additional association data, which he/she believes may be relevant to the clinical presentation (e.g., smoking history).
  c. The ER physician selects the automated option, in which the program 110 provides a list of strongly associated data, which the ER physician responds to as present, absent, or unsure.

Step 306: The association database 114 is queried by the program 110 in accordance with the data provided and presents the ER physician with a hierarchical list of diseases which are consistent with the generic association data.

Step 307: This hierarchical list also has a statistical probability associated with each of the listed diseases, as it relates to the defined patient population.

Note: The defined patient population represents the population of patients used in the association data analysis. As an example, the query performed by the program 110 can restrict analysis to specific patient characteristics (i.e., based upon age, gender, body habitus, etc.)

Step 308: The ER physician may subsequently request correlation by the program 110 of this hierarchical differential diagnosis with the individual patient's genetic make-up.

Step 309: The revised differential diagnosis provided by the program 110 represents a composite statistical analysis of the association and patient-specific databases.

To illustrate the steps in the method in performing an embodiment consistent with the present invention, a clinical example is provided to show how association data is identified, recorded, displayed, and analyzed by the program 110. In this example, the following steps take place in the sequential clinical care of the patient:

Step 400: Patient presents to office of primary care physician (PCP) due to abdominal pain.

Step 401: PCP orders a series of laboratory and imaging tests for diagnosis.

Step 402: PCP prescribes medication for symptomatic relief.

Step 403: Pharmacist alerts PCP of potential drug reaction.

Step 404: PCP adjusts medication order.

Step 405: Patient returns to emergency room due to increased abdominal pain.

Step 406: Repeat laboratory and imaging tests are performed.

Step 407: Surgeon is consulted and makes presumptive diagnosis of acute cholecystitis.

Step 408: Surgeon schedules patient for emergent cholecystectomy.

Step 409: Small perforation in gall bladder wall found at surgery.

Step 410: Patient placed on a course of post-operative antibiotics.

Step 411: Patient discharged to home 3 days later.

Step 412: Patient returns to emergency room post-operative day nine (9).

Step 413: Repeat imaging and laboratory tests are performed.

Step 414: Surgical consultation is performed.

Step 415: Percutaneous abscess drainage is performed.

Step 416: Patient discharged from hospital (day 17 after cholecystectomy).

Step 417: Patient returns to surgeon as outpatient for re-evaluation.

The data recorded during these steps include the following:
1. PCP history and physical (H & P) report:
  a. family history of gastric carcinoma
  b. past medical history of gastritis
  c. abdominal pain of increasing severity
  d. localized tenderness over epigastrum

| Associated Data: Abdominal Pain | Type of Association | Strength of Association | Data Source | Author |
|---|---|---|---|---|
| Localized tenderness on physical exam | Connected to | Definitely associated | H & P | PCP |
| Past medical history of gastritis | Causation | Likely associated | H & P | PCP |
| Family history of gastric cancer | Connected to | Possibly associated | H & P | PCP |

2. Laboratory test data:
  a. Elevated white blood cell (WBC) count
  b. Elevated bilirubin and amylase

| Associated Data: Abdominal Pain | Type of Association | Strength of Association | Data Source | Author |
|---|---|---|---|---|
| Elevated WBC | Connected to | Likely associated | Laboratory | PCP |
| Elevated Bilirubin | Connected to | Possibly associated | Laboratory | PCP |
| Elevated Amylase | Connected to | Possibly associated | Laboratory | PCP |

3. Imaging test data (CT):
  a. Gallstones
  b. Gastric wall thickening
  c. Bowel dilatation
  d. Ascites

| Associated Data: Abdominal Pain | Type of Association | Strength of Association | Data Source | Author |
|---|---|---|---|---|
| Gallstones | Causation | Likely associated | Abdominal CT | Radiologist |
| Gastric wall thickening | Causation | Possibly associated | Abdominal CT | Radiologist |
| Bowel dilatation | Connected to | Possibly associated | Abdominal CT | Radiologist |
| Ascites | Connected to | Possibly associated | Abdominal CT | Radiologist |

4. ER physician consultation note:
   a. Worsening abdominal pain with anorexia
   b. Localized tenderness and rebound on physical exam

| Associated Data: Abdominal Pain | Type of Association | Strength of Association | Data Source | Author |
|---|---|---|---|---|
| Abdominal Pain | Equivalence | Definitely associated | Consultation Note | ER Physician |
| Tenderness and Rebound | Connected to | Definitely associated | Physical Exam Consultation Note | ER Physician |

5. Imaging test data (Ultrasound):
   a. Gallstones
   b. Wall edema
   c. Positive Murphy's sign

| Associated Data: Abdominal Pain | Type of Association | Strength of Association | Data Source | Author |
|---|---|---|---|---|
| Gallstones | Causation | Definitely associated | Ultrasound | Radiologist |
| Wall edema | Connected to | Definitely associated | Ultrasound | Radiologist |
| Positive Murphy's sign | Equivalence | Definitely associated | Ultrasound | Radiologist |

6. Surgical consultation note:
   a. Diagnosis: Acute cholecystitis

| Associated Data: Abdominal Pain | Type of Association | Strength of Association | Data Source | Author |
|---|---|---|---|---|
| Cholecystitis | Causation | Definitely associated | Physical exam | Surgeon |

7. Operative note:
   a. Inflamed gall bladder with wall perforation.
   b. Ascites
   c. Cholelithiasis

| Associated Data: Abdominal Pain | Type of Association | Strength of Association | Data Source | Author |
|---|---|---|---|---|
| Perforated Cholecystitis | Causation | Definitely associated | Operative Note | Surgeon |
| Ascites | Connected to | Definitely associated | Operative Note | Surgeon |
| Cholelithiasis | Connected to | Definitely associated | Operative Note | Surgeon |

8. ER physician consultation note:
   a. Fever and worsening abdominal pain
   b. Suspect post-operative abscess

| Associated Data: Abdominal Pain | Type of Association | Strength of Association | Data Source | Author |
|---|---|---|---|---|
| Fever | Connected to | Definitely associated | Consultation Note | ER Physician |
| Abscess | Causation | Likely associated | Consultation Note | ER Physician |

Surgical consultation note suggests that fever is likely associated with abdominal pain and that abscess is definitely associated with abdominal pain.

9. Imaging test data (CT):
   a. Abscess gall bladder fossa
   b. Bowel dilatation (ileus)
   c. Ascites

| Associated Data: Abdominal Pain | Type of Association | Strength of Association | Data Source | Author |
|---|---|---|---|---|
| Abscess | Causation | Definitely associated | Abdominal CT | Radiologist |
| Ileus | Connected to | Definitely associated | Abdominal CT | Radiologist |
| Ascites | Connected to | Definitely associated | Abdominal CT | Radiologist |

The above example would show the types of associations that are recorded during an actual clinical situation, and the above review and analyses can be performed by the program 110 to ensure that other data is retrieved to assist the medical professional in diagnosis and treatment of the patient.

Thus, the ability to record, track, and analyze multiple association links across multiple patients, end-users, and institutions provides an intuitive means for understanding the relationship between disparate medical data. The ultimate goal is to use this newfound medical knowledge to create best practice guidelines to improve clinical outcomes.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of defining an association between different data elements from disparate sources of data, comprising:
   receiving, and storing in a database, an input from a user linking a plurality of different data elements from disparate data sources;
   receiving a further input from the user on specific association relationships between said plurality of different data elements, and on a comparative statistical strength of each of said specific association relationships, and storing said further input in said database;
   wherein said comparative statistical strength includes a degree of relationship of each of said specific association relationships between said plurality of different data elements, said degree of relationship of each said specific association relationships between said plurality of different data elements being chosen from the following options: a possible relationship, a likelihood of a relationship, and a definite relationship;
   receiving a still further input from the user on how said plurality of different data elements are associated, and storing said still further input in said database;
   wherein said still further input from the user on how said plurality of different data elements are associated includes at least one of the following options: a cause and effect relationship, essentially equivalent, or definitely different, wherein said input, said further input, and said still further input are carried out through an input device including at least one of an electronic stylus, a computer mouse, or a keyboard;

analyzing, using a processor, said plurality of different data elements and said specific association relationships with respect to clinical data on a patient inputted into said database, to further define said specific association relationships; and validating said specific association relationships based on said analysis of said plurality of different data elements with respect to said clinical data, and on a clinical diagnosis of a patient.

2. The method according to claim 1, further comprising:
creating, and storing in said database, automated specific association relationships with said plurality of different data elements.

3. The method according to claim 1, wherein said specific association relationships include at least one of an equivalence, a temporal association, an approximation, a causation, and a lack of relationship.

4. The method according to claim 3, further comprising:
automatically adding new specific association relationships to said database when said new specific association relationships are identified by the user.

5. The method according to claim 4, further comprising:
automatically generating a query to said database to identify any other previously defined specific association relationships related to said different data elements being linked.

6. The method according to claim 5, further comprising:
modifying, and storing in said database, any said previously defined specific association relationships to include any new data on at least said specific association relationships or said different data elements.

7. The method according to claim 6, further comprising:
creating, and storing in said database, a user context-specific association profile to prioritize said different data elements from said disparate data sources, and prioritize said specific association relationships.

8. The method according to claim 7, wherein said specific association relationships are displayed differently for each said user based on occupational and experiential differences.

9. The method according to claim 7, further comprising:
creating, and storing in said database, computer-program derived specific association relationships.

10. The method according to claim 9, wherein said specific association relationships are recorded in multiple databases in multiple facilities, and can be cross-referenced.

11. The method according to claim 10, further comprising:
providing a feedback mechanism to users when conflicting specific association relationships are recorded in said database;
recording differing specific association relationships by different users in said database; and
displaying said differing specific association relationships to users, on a display.

12. The method according to claim 11, further comprising:
providing an automated alert to users and authors, using a predetermined communication protocol, such that said users and authors can amend their specific association relationships in light of said conflicting specific association relationships.

13. The method according to claim 11, further comprising:
storing in said database, said clinical data on a patient; and
cross-referencing said stored different data elements to further delineate said specific association relationships.

14. The method according to claim 13, further comprising:
displaying on a display, said clinical diagnosis of the patient;
reviewing and analyzing discrepancies in said conflicting specific association relationships, for accuracy; and
storing in said database, a quantitative measure of diagnostic accuracy which reflects any of said discrepancies.

15. The method according to claim 14, wherein a result of said cross-reference of said different data elements and said clinical diagnosis of the patient, results in a validation of said specific association relationships.

16. The method according to claim 15, further comprising:
conducting a retrospective and/or prospective review and analysis of said database.

17. The method according to claim 16, further comprising:
developing context and user-specific medical educational programs using said database.

18. The method according to claim 17, further comprising:
searching a patients electronic medical record for unrecognized specific association relationships; and
correlating said specific association relationships with said multi-institutional databases to document specific association relationships within said electronic medical record.

19. The method according to claim 18, further comprising:
correlating generic specific association relationships derived from said database, with personalized data derived from genetic data from the patient.

20. The method according to claim 19, further comprising:
providing a hierarchical differential diagnosis of the patient based upon said correlation.

21. The method according to claim 10, wherein said different data elements include at least one of: different data elements defining said specific association relationships, said disparate data sources of said different data elements, types of specific association relationships, statistical strengths of said specific association relationships, authors of said specific association relationships, date and time of recordation of said different data elements in said database, degree of database occurrence of said different data elements, previously defined specific association relationships, and a response to said computer program-derived specific association relationships.

22. A computer system which defines an association between different data elements from disparate sources of data, comprising:
at least one memory which contains at least one program which comprises the steps of:
receiving, and storing in a database, an input from a user linking a plurality of different data elements from disparate data sources;
receiving a further input from the user on specific association relationships between said plurality of different data elements, and on a comparative statistical strength of each of said specific association relationships, and storing said further input in said database;
wherein said comparative statistical strength includes a degree of relationship of each of said specific association relationships between said plurality of different data elements, said degree of relationship of each said specific association relationships between said plurality of different data elements being chosen from the following options: a possible relationship, a likelihood of a relationship, and a definite relationship;
receiving a still further input from the user on how said plurality of different data elements are associated, and storing said still further input in said database;

wherein said still further input from the user on how said plurality of different data elements are associated includes at least one of the following options: a cause and effect relationship, essentially equivalent, or definitely different, wherein said input, said further input, and said still further input are carried out through an input device including at least one of an electronic stylus, a computer mouse, or a keyboard;

analyzing, using a processor, said plurality of different data elements and said specific association relationships with respect to clinical data on a patient inputted into said database, to further define said specific association relationships; and validating said specific association relationships based on said analysis of said plurality of different data elements with respect to said clinical data, and on a clinical diagnosis of a patient; and at least one processor which executes the program.

23. A non-transitory computer readable medium containing executable code which defines an association between different data elements from disparate sources of data, comprising:

receiving, and storing in a database, an input from a user linking a plurality of different data elements from disparate data sources;

receiving a further input from the user on specific association relationships between said plurality of different data elements, and on a comparative statistical strength of each of said specific association relationships, and storing said further input in said database;

wherein said comparative statistical strength includes a degree of relationship of each of said specific association relationships between said plurality of different data elements, said degree of relationship of each said specific association relationships between said plurality of different data elements being chosen from the following options: a possible relationship, a likelihood of a relationship, and a definite relationship;

receiving a still further input from the user on how said plurality of different data elements are associated, and storing said still further input in said database;

wherein said still further input from the user on how said plurality of different data elements are associated includes at least one of the following options: a cause and effect relationship, essentially equivalent, or definitely different, wherein said input, said further input, and said still further input are carried out through an input device including at least one of an electronic stylus, a computer mouse, or a keyboard;

analyzing, using a processor, said plurality of different data elements and said specific association relationships with respect to clinical data on a patient inputted into said database, to further define said specific association relationships; and validating said specific association relationships based on said analysis of said plurality of different data elements with respect to said clinical data, and on a clinical diagnosis of a patient.

24. A computer-implemented method of defining an association between different data elements from disparate sources of data, comprising:

receiving, and storing in a database, an input from a user linking a plurality of different data elements from disparate data sources;

receiving a further input from the user on specific association relationships between said plurality of different data elements, and on a comparative statistical strength of each of said specific association relationships, and storing said further input in said database, said specific association relationships including at least one of an equivalence, a temporal association, an approximation, a causation, and a lack of relationship;

wherein said input and said further input are carried out through an input device, wherein said comparative statistical strength includes a degree of relationship of each of said specific association relationships between said plurality of different data elements, said degree of relationship of each said specific association relationships between said plurality of different data elements, including at least one of a possible relationship, a likelihood of a relationship, a definite relationship, and a cause and effect relationship;

analyzing, using a processor, said plurality of different data elements and said specific association relationships with respect to clinical data on a patient inputted into said database, to further define said specific association relationships;

validating said specific association relationships based on said analysis of said plurality of different data elements with respect to said clinical data, and on a clinical diagnosis of a patient;

automatically adding new specific association relationships to said database when said new specific association relationships are identified by the user;

automatically generating a query to said database to identify any other previously defined specific association relationships related to said different data elements being linked;

modifying, and storing in said database, any said previously defined specific association relationships to include any new data on at least said specific association relationships or said different data elements;

creating, and storing in said database, a user context-specific association profile to prioritize said different data elements from said disparate data sources, and prioritize said specific association relationships;

creating, and storing in said database, computer-program derived specific association relationships;

wherein said specific association relationships are recorded in multiple databases in multiple facilities, and can be cross-referenced, the computer-implemented method further comprising:

providing a feedback mechanism to users when conflicting data on said specific association relationships is recorded in said database;

recording differing specific association relationships by different users in said database; and displaying said differing specific association relationships to users, on a display.

* * * * *